(12) United States Patent
Hayashi (10) Patent No.: US 9,155,455 B2
(45) Date of Patent: Oct. 13, 2015

(54) ENDOSCOPE GAS DELIVERY SYSTEM (75) Inventor: Kentaro Hayashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1130 days.

(21) Appl. No.: 13/179,431

(22) Filed: Jul. 8, 2011

(65) Prior Publication Data

US 2012/0016293 A1    Jan. 19, 2012

(30) Foreign Application Priority Data

Jul. 14, 2010 (JP) .................................. 2010-159344
May 31, 2011 (JP) .................................. 2011-121968

(51) Int. Cl.
*A61M 37/00* (2006.01)
*A61B 1/015* (2006.01)
*A61B 1/12* (2006.01)

(52) U.S. Cl.
CPC ................. *A61B 1/015* (2013.01); *A61B 1/126* (2013.01)

(58) Field of Classification Search
CPC ..................... A61M 13/003; A61M 2005/006; A61M 2205/3334; A61M 2205/3344; A61M 1/126; A61M 1/015
USPC .......................................... 604/26, 23, 30, 24
See application file for complete search history.

(56) References Cited

U.S. PATENT DOCUMENTS

| 7,476,213 | B2 | 1/2009 | Uesugi et al. | |
| 2006/0004322 | A1* | 1/2006 | Uesugi et al. | .................. 604/26 |
| 2007/0244363 | A1* | 10/2007 | Sano et al. | .................... 600/158 |
| 2008/0200759 | A1 | 8/2008 | Niwa et al. | |
| 2011/0034862 | A1 | 2/2011 | Williams, Jr. et al. | |
| 2012/0157770 | A1 | 6/2012 | Williams, Jr. et al. | |

FOREIGN PATENT DOCUMENTS

CN     2927982 Y    8/2007
CN     101243965 A  8/2008
(Continued)

OTHER PUBLICATIONS

An Office Action; "Notice of Reasons for Rejection," issued by the Japanese Patent Office on Mar. 19, 2014, which corresponds to Japanese Patent Application No. 2011-121968 and is related to U.S. Appl. No. 13/179,431; with English language translation.

(Continued)

*Primary Examiner* — Bhisma Mehta
*Assistant Examiner* — Brandy S Lee
(74) *Attorney, Agent, or Firm* — Studebaker & Brackett PC (57) ABSTRACT

Gases are smoothly and automatically switched when using two gas supply sources, that is, an air pump and a carbon dioxide gas cylinder. By using a gas supply flow rate adjusting unit, a carbon dioxide gas is supplied to an endoscope, and a gas using a carbon dioxide gas and water are delivered. When the remaining amount of the carbon dioxide gas of the cylinder is detected and the detected pressure of the carbon dioxide gas becomes less than a predetermined value, the air pump is rotated to supply pressurized air. The rotation number of the air pump is controlled, and the same amount of pressurized air is supplied as that of the supplied carbon dioxide gas. The switching to the pressurized air is automatically performed. The supply amounts before and after the switching become equal to each other, and a surgical operator does not feel any discomfort.

18 Claims, 9 Drawing Sheets

(56) References Cited

FOREIGN PATENT DOCUMENTS

| | | |
|---|---|---|
| CN | 101312763 A | 11/2008 |
| CN | 101485591 A | 7/2009 |
| JP | H05-220104 A | 8/1993 |
| JP | 2006-014961 A | 1/2006 |
| JP | 2006-181108 A | 7/2006 |
| JP | 2006-325814 A | 12/2006 |

OTHER PUBLICATIONS

The First Office Action issued by the State Intellectual Property Office of People's Republic of China on May 4, 2014, which corresponds to Chinese Patent Application No. 201110191585.6 and is related to U.S. Appl. No. 13/179,431; with English language translation.

* cited by examiner

ENDOSCOPE GAS DELIVERY SYSTEM

BACKGROUND OF THE INVENTION

1. Field of the Invention

The present invention relates to an endoscope gas delivery system.

2. Description of the Related Art

A medical endoscope includes an illumination window, an observation window, and a clamp outlet provided at a front end of an insertion section. At the time of using the endoscope, the insertion section is inserted into a body cavity of a subject. Then, the inside of the body cavity is irradiated with illumination light from the illumination window, and is observed from the observation window. When a diseased area or the like is found, a high frequency treatment tool, a clamp, or the like is inserted through a clamp channel, and the diseased area is treated by the clamp or the like exiting the clamp outlet.

For this reason, the endoscope system includes a light source device, a processor, and a monitor as well as the endoscope. Furthermore, if necessary, a high frequency power supply device, a VTR, a printer, or the like is attached to the endoscope system. The various devices are installed in a cart together with the endoscope. The cart includes a plurality of stages of shelves on which various devices are installed, and is configured to be movable. The endoscope system is carried to a clinical site by the cart, and an examination or a treatment using the endoscope is performed.

The inside of the body cavity is irradiated with the illumination light, output from the light source of the light source device, through a light guide from the illumination window. An imaging unit is disposed inside a front end of the insertion section at a position facing the observation window. The imaging unit images the inside of the body cavity from the observation window. Image signals output from the imaging unit are output to the processor through a universal cord. The processor processes the image signals and displays the result on the monitor.

When an examination or a treatment is performed by the endoscope, a surgical operator (an operator) controls various devices connected to the endoscope. For example, the light source device adjusts the light amount of the light source so as to sharpen the image inside the body cavity displayed on the monitor. Furthermore, when the high frequency treatment tool is used, the voltage or the current of the high frequency power supply is appropriately controlled, and a safe and efficient treatment is performed.

The endoscope includes supply paths for a pressurized liquid and a pressurized gas. The pressurized liquid is used for various purposes. For example, the pressurized liquid is used to clean the observation window, to clean the inner wall of the body cavity, to spray a chemical liquid, and to perfuse a liquid through an organ or a tissue. The pressurized gas is used to expand the inside of the body cavity and remove liquid droplets of the cleaned observation window. As a pressurization source for a liquid and a gas, for example, an air pump is used. When the pressurized gas is supplied, the air pump is driven. Furthermore, in order to pressurize a liquid during liquid delivery, the pressurized air is supplied from the air pump to the liquid delivery tank. The air pump is generally built in the light source device. Furthermore, the liquid delivery tank is separably attached to the light source device. In addition to the on/off state of the air pump, the rotation number thereof is also controlled, so that the pressure and the flow rate of the pressurized air are changed.

In recent years, a pressurized gas source of a carbon dioxide gas ($CO_2$) has been commercialized instead of the pressurization of air using the air pump. The carbon dioxide gas is desirable from the viewpoint that the carbon dioxide gas is more easily absorbed to the body than air, safety improves, and the burden on the patient is reduced. When the carbon dioxide gas is used as the pressurized gas source, a carbon dioxide gas supply device using a carbon dioxide gas cylinder is used. The carbon dioxide gas supply device is separably connected to a gas delivery passage of the endoscope, and supplies the carbon dioxide gas from the carbon dioxide gas cylinder in a depressurized state.

For example, JP2006-14961A proposes a gas delivery system in which a carbon dioxide gas cylinder is used as a pressurized gas source in addition to an air pump. In the gas delivery system, pressurized air may be supplied from the air pump in addition to the carbon dioxide gas from the carbon dioxide gas cylinder.

SUMMARY OF THE INVENTION

However, in the endoscope gas delivery system disclosed in JP2006-14961A, the pressurized air may be selectively supplied in addition to the carbon dioxide gas, but the switching is performed by the operator. Therefore, although a cylinder remaining amount alarm is generated when the carbon dioxide gas is consumed, the switching needs to be performed by manually.

The present invention is made to solve the above-described problems and it is an object to provide an endoscope gas delivery system capable of selectively switching to pressurized air using a pump and a gas of a cylinder and continuously delivering a gas by automatically switching to the pressurized air when the remaining amount of the gas of the cylinder becomes a predetermined amount or less during the supply of the gas of the cylinder.

In order to attain the above-described object, according to an aspect of the present invention, there is provided an endoscope gas delivery system including: a pressurized air supply device that includes an air pump generating pressurized air and a pressurized air supply flow rate adjusting unit adjusting a supply flow rate of the pressurized air and supplies the pressurized air to the conduit connection portion connected with a gas supply tube of a universal cord; a gas supply device that includes a gas cylinder supplying a gas and a gas supply flow rate adjusting unit adjusting the supply flow rate of the gas and supplies the gas to the conduit connection portion; and a gas switching control section that controls the pressurized air supply device and the gas supply device, delivers one of the pressurized air and the gas to the conduit connection portion, and performs a switching control using a supply flow rate setting value of the other of the pressurized air and the gas before the switching.

Furthermore, the endoscope gas delivery system may further include: a supply flow rate setting value storing section that stores the supply flow rate setting value of the pressurized gas supply flow rate adjusting unit and the supply flow rate setting value of the gas supply flow rate adjusting unit, wherein the gas switching control section may perform the switching by reading out the supply flow rate setting value before the switching from the supply flow rate setting value storing section. Further, the gas may be a carbon dioxide gas, and the gas supply device may be first used from the initial setting.

The gas supply flow rate adjusting unit may include: a depressurizing mechanism in which first and second depressurizing valves are connected to each other in series, a pressure gauge that is provided near an inlet of the first depressurizing valve, a flow rate control valve that is provided near an outlet of the second depressurizing valve, and a gas supply control section that controls the flow rate control valve based on the supply flow rate setting value. Further, the pressurized gas supply flow rate adjusting unit may include a pump driving circuit that controls the rotation number of the air pump.

When the pressure of the pressure gauge becomes a first value PS1, the gas supply control section may transmit a gas switching signal to the gas switching control section, and the gas switching control section may turn off the flow rate control valve and drive the air pump to switch the carbon dioxide gas to the pressurized air. Furthermore, when the pressure of the pressure gauge becomes a second value PS2 (PS2>PS1), the gas supply control section may idly rotate the air pump. In this case, the switching may be performed in a short time.

The endoscope gas delivery system may further include: a concentration sensor that detects the concentration of the carbon dioxide gas, wherein when the concentration of the concentration sensor becomes a first value CS1, a gas switching signal may be transmitted to the gas switching control section, and the gas switching control section may turn off the flow rate control valve and drive the air pump to switch the carbon dioxide gas to the pressurized air. In this case, the carbon dioxide gas and the pressurized air may be switched based on the concentration of the carbon dioxide gas inside the body cavity or the environmental atmosphere. Furthermore, when the detected concentration of the concentration sensor becomes a second value CS2 (CS2<CS1), the gas supply control section may idly rotate the air pump. Furthermore, when the detected concentration of the concentration sensor becomes a third value CS3 (CS3<CS2), the gas supply control section may transmit a gas switching signal to the gas switching control section, stop the air pump, and turn on the flow rate control valve. In this case, when the concentration of the carbon dioxide gas returns within an appropriate range, the pressurized air is automatically switched to the carbon dioxide gas.

The endoscope gas delivery system may further include: an imaging unit that is disposed to face an observation window of a front end of the insertion section; and a processor that receives an image signal from the imaging unit, performs an image process on the imaging signal, and displays the result on a monitor, wherein a control section of the processor may constitute the gas switching control section. In this case, the gas switching control section may be configured through software using the control section of the processor, and the configuration may become simple since it is not necessary to further provide a new controller.

Furthermore, the conduit connection portion may form a chamber between the conduit connection portion and a conduit connection connector, and include a relief valve communicative connected with the chamber and releasing a gas when the pressure of the chamber becomes a predetermined pressure or more.

According to the present invention, there are provided two gas supply sources, that is, the air pump and the gas cylinder, and the pressurized air is automatically switched before the remaining amount of the gas in the gas cylinder decreases to a predetermined pressure at which the gas cannot be supplied, so that the gas may be automatically and continuously supplied. Moreover, since the other gas is automatically switched at a pressure before the switching, the gas or the liquid may be smoothly delivered to the endoscope without causing any discomfort to the surgical operator.

DESCRIPTION OF THE PREFERRED EMBODIMENTS

Figure 1:
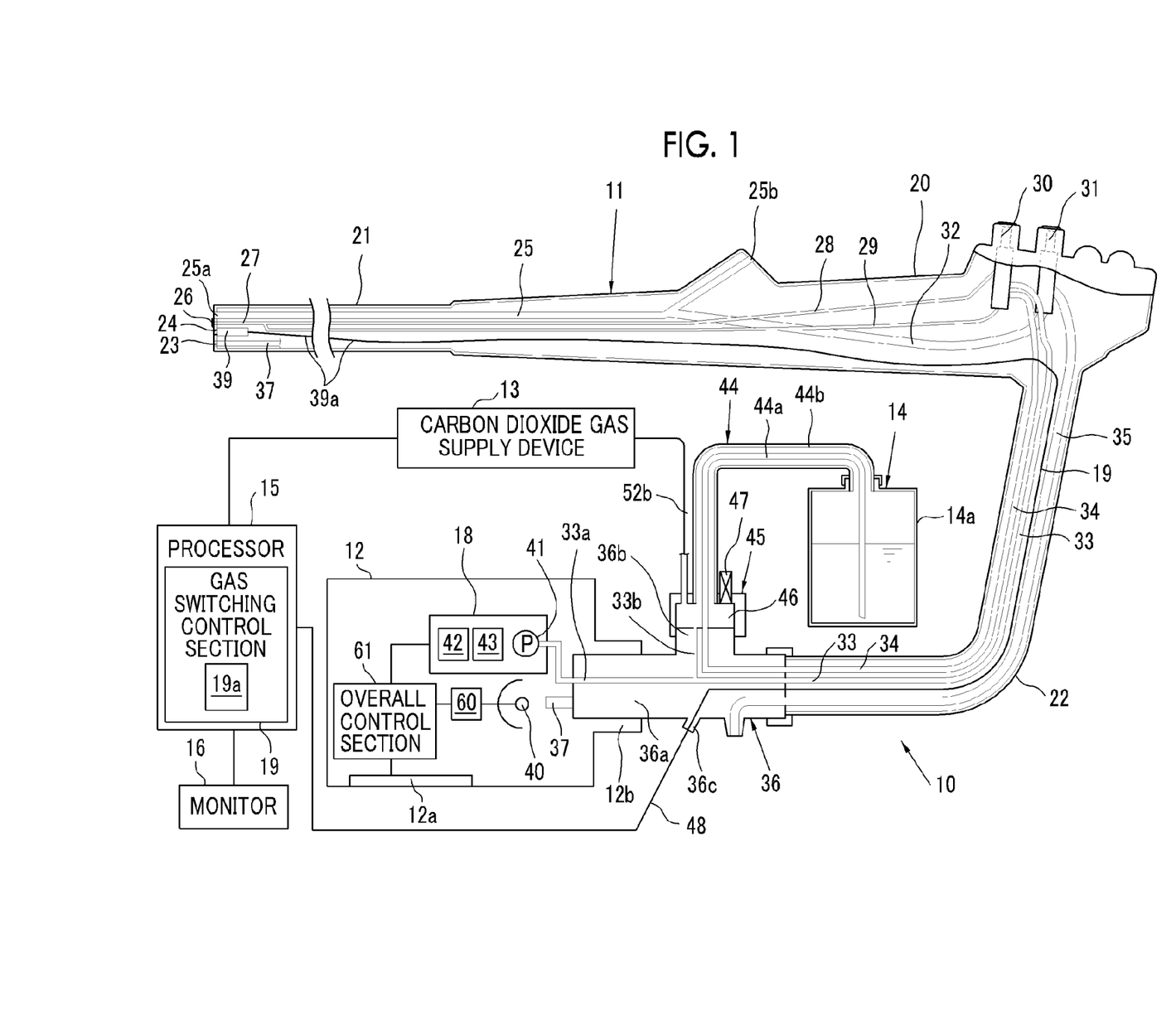
FIG. 1 is a schematic diagram illustrating an endoscope gas delivery system of the present invention.
Figure 2:
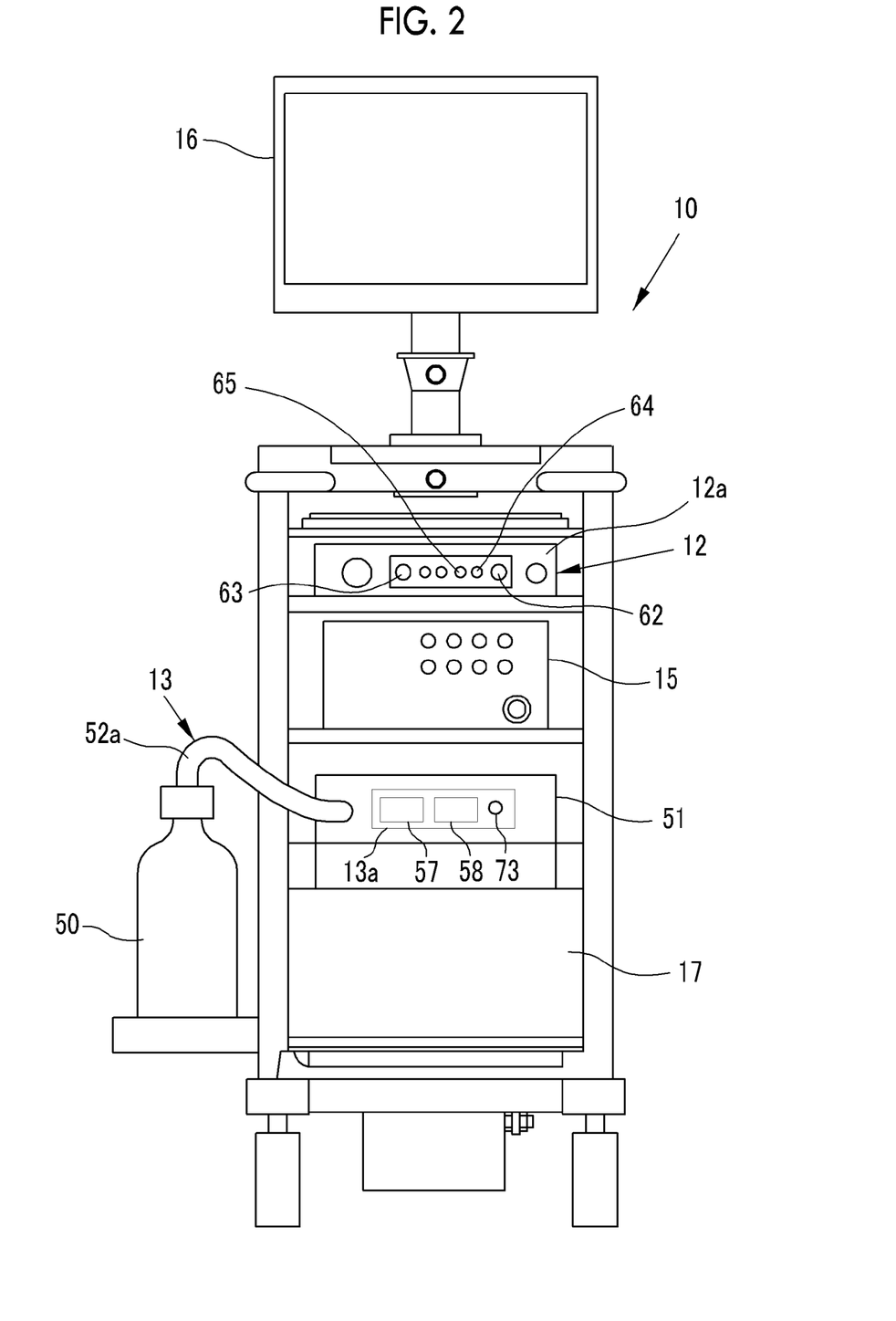
FIG. 2 is a front view illustrating an endoscope system in which devices relating to an endoscope are received in a cart.

As shown in FIG. 1, an endoscope system 10 includes an endoscope 11, a light source device 12, a carbon dioxide gas supply device 13, a liquid delivery device 14, a processor 15, a monitor 16, and a cart 17 (refer to FIG. 2).

As shown in FIG. 2, the cart 17 holds the devices 12 to 16, and is configured to be movable. The cart 17 is provided with various devices relating to the endoscope in addition to the devices 12 to 16 if necessary. Furthermore, the carbon dioxide gas supply device 13 or the liquid delivery device 14 may be provided at the outside separately from the cart 17.

As shown in FIG. 1, the endoscope 11 includes a main body manipulation section 20, an insertion section 21, and a universal cord 22. The insertion section 21 is provided to be connected to the main body manipulation section 20, and is inserted into a body cavity of a subject. The front end of the insertion section 21 is provided with an illumination window 23, an observation window 24, a clamp outlet 25a, and a gas/water delivery nozzle 26. One end of a clamp insertion channel 25 inserted through the insertion section 21 serves as the clamp outlet 25a, and the other end thereof serves as a clamp inlet 25b that is opened from the main body manipulation section 20. One end of a suction path 32 is connected to an intermediate portion of the clamp insertion channel 25, and the other end of the suction path 32 is connected to a suction valve 31.

The gas/water delivery nozzle 26 is disposed near the observation window 24. The gas/water delivery nozzle 26 is communicative connected with a fluid passage 27 inside the insertion section 21. The fluid passage 27 is separated into a gas delivery path 28 and a water delivery path 29 from the intermediate portion of the insertion section 21, and the branched paths are connected to a gas/water delivery valve 30 of the main body manipulation section 20. For example, when the button of the gas/water delivery valve 30 is fully pushed, a liquid is delivered, so that the liquid is ejected from the nozzle 26 toward the observation window 24. Accordingly, the observation window 24 is cleaned. Furthermore, for example, when the button of the gas/water delivery nozzle 26 is half pushed, a gas is delivered, so that the gas is ejected from the nozzle 26 toward the observation window 24. Accordingly, liquid droplets adhering to the observation window 24 scatter.

The gas/water delivery valve 30 is connected with a gas supply tube 33 and a liquid supply tube 34. Furthermore, the suction valve 31 is connected with a suction tube 35. The gas supply tube 33, the liquid supply tube 34, and the suction tube 35 extend to the universal cord 22. The front end of the universal cord 22 is provided with a connector 36. The connector 36 includes a light source connection portion 36a, a conduit connection portion 36b, and a cord connection portion 36c. The light source connection portion 36a is separably connected to the light source device 12 through a tube sleeve 12b. Furthermore, the conduit connection portion 36b is connected to a liquid delivery tank 14a via a conduit connection connector 45 and a multi-conduit 44. Furthermore, the cord connection portion 36c is connected to the processor 15 through a connection cord 48.

The liquid delivery device 14 includes the liquid delivery tank 14a and the multi-conduit 44. One end of the multi-conduit 44 is connected to the liquid delivery tank 14a, and the other end thereof is connected to the connector 36 of the light source device 12 through the conduit connection connector 45.

The gas supply tube 33 is branched inside the connector 36. One branch tube 33a extends to the light source connection portion 36a, and is connected to an air pump 41. The other branch tube 33b is opened from the conduit connection portion 36b. The conduit connection portion 36b is separably connected with the conduit connection connector 45 of the multi-conduit 44. Then, when the conduit connection connector 45 is connected to the conduit connection portion 36b, a chamber 46 is formed therein. The branch tube 33b is opened from the chamber 46. The conduit connection connector 45 is attached with a relief valve 47. The relief valve 47 releases the gas therein when the pressure inside the liquid delivery tank 14a and the chamber 46 becomes higher than a predetermined value due to the continuous operation of the air pump 41, so that the pressure inside the liquid delivery tank 14a and the chamber 46 is maintained at a predetermined pressure. Furthermore, the relief valve may be attached to the connector 36 or the liquid delivery device 14 instead of the conduit connection connector 45.

The multi-conduit 44 is formed as a double tube with an inner tube 44a and an outer tube 44b. Then, the other end of the inner tube 44a is opened near the bottom surface of the liquid delivery device 14. Accordingly, the opening of the inner tube 44a is normally inserted in a liquid. The other end of the outer tube 44b is connected to the upper portion of the liquid delivery tank 14a so as to be positioned above the liquid surface of the liquid delivery tank 14a. The inner tube 44a is communicative connected with the liquid supply tube 34 when the conduit connection connector 45 is connected to the conduit connection portion 36b, and the outer tube 44b is communicative connected with the chamber 46. When a carbon dioxide gas or pressurized air is introduced into the chamber 46, the liquid surface of the liquid delivery tank 14a is pressurized by the carbon dioxide gas or the pressurized air, and the liquid may be delivered to the gas/water delivery valve 30 through a liquid delivery operation of the gas/water delivery valve 30.

An imaging unit 39 is disposed at a position facing the observation window 24 inside the front end of the endoscope 11. The inside of the body cavity is imaged by the imaging unit 39 through the observation window 24. Image signals are transmitted to the processor 15 through a signal cord 39a and a connection cord 48. The signal cord 39a reaches a cord connection portion 36c of the connector 36 through the inside of the insertion section 21, the main body manipulation section 20, and the universal cord 22. The cord connection portion 36c is connected with the connection cord 48, so that the signal cord 39a and the connection cord 48 are electrically connected to each other. The connection cord 48 is connected to the processor 15. The processor 15 performs a predetermined signal process on the image signals, and displays the endoscope image on the monitor 16.

The light source device 12 includes a pressurized air supply device 18, a light source lamp (an illumination light source) 40, a light source control section 60, an air pump 41, a rotation number control section 43, a pump driving circuit 42, an overall control section 61, and an operation panel 12a. When the light source connection portion 36a is connected to the light source device 12, an input end of a light guide 37 protruding from the light source connection portion 36a faces the light source lamp 40, so that illumination light is input to the light guide 37. The output end of the light guide 37 is positioned at the illumination window 23 of the front end of the insertion section 21, so that the inside of the body cavity is irradiated with the illumination light from the illumination window 23.

Figure 3:
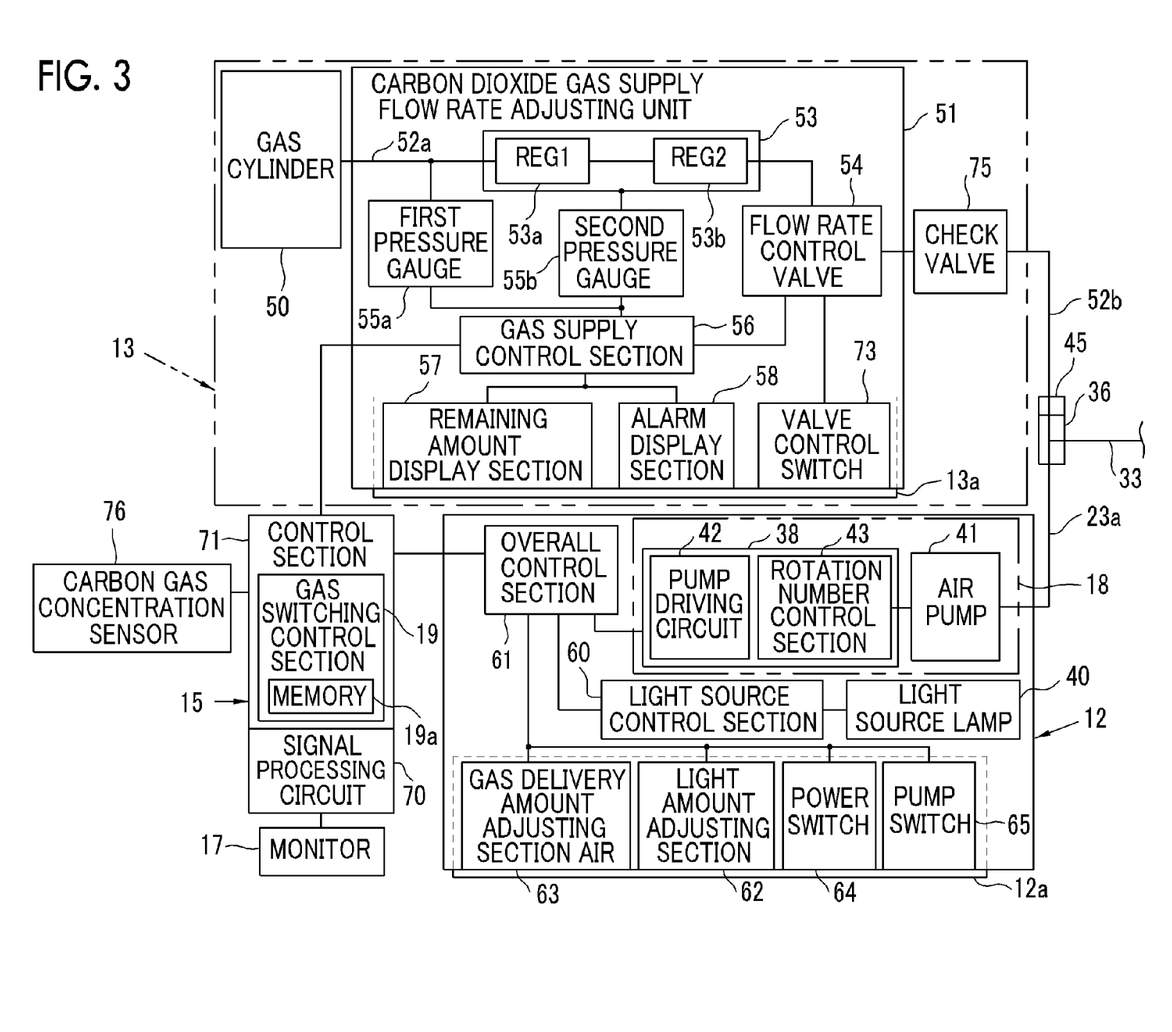
FIG. 3 is a block diagram illustrating a configuration of a light source device, a processor, and a carbon dioxide gas supply device.
Figure 4:
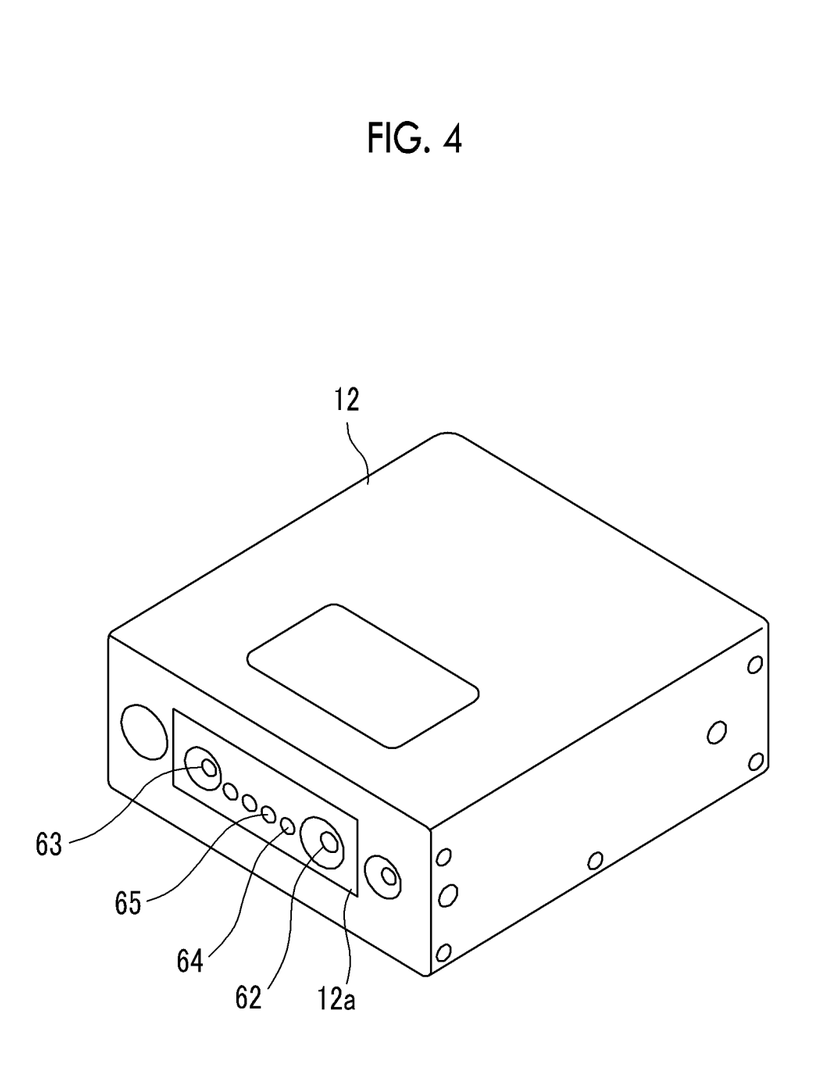
FIG. 4 is a perspective view illustrating an appearance of the light source device.

As shown in FIG. 4, the front surface of the light source device 12 is provided with an operation panel 12a. The operation panel 12a is provided with a light amount adjusting section 62, a gas delivery amount adjusting section 63, a power switch 64, and a pump switch 65. The light amount adjusting section 62 includes an operation button (or an operation handle), and may instruct an increase or decrease in the amount of light through a push operation or a rotation operation. The signal instructing an increase or decrease in the amount of light through the operation handle is transmitted to the overall control section 61 (refer to FIG. 3). The overall control section 61 controls the light source control section 60 based on the light amount increase/decrease instruction signal, and continuously changes the light amount of the light source lamp 40. Therefore, a surgical operator may adjust the brightness of the endoscope image displayed on the monitor 16 and observe the inside of the body cavity under the optimal illumination environment by adjusting the light amount of the light source lamp 40 while seeing the endoscope image displayed on the monitor 16.

As shown in FIG. 3, the endoscope gas delivery system of the present invention includes the carbon dioxide gas supply device 13, the pressurized air supply device 18, and a gas switching control section 19.

The pressurized air supply device 18 includes the air pump 41 and a pressurized air supply flow rate adjusting unit 38. The air pump 41 is rotationally driven by a motor, and generates pressurized air. The pressurized air supply flow rate adjusting unit 38 is configured as the pump driving circuit 42 including the rotation number control section 43 of a motor. The rotation number control section 43 controls the rotation number of a motor (not shown) connected to the air pump 41, and switches the ejection flow rate of the air pump 41 to three stages, for example, a flow rate H, a flow rate M, and a flow rate L. Furthermore, the ejection flow rate of the air pump 41 may be adjusted in a single stage, but the air pump may be practically used without any problem in three stages, that is, a large flow rate (flow rate H), a middle flow rate (flow rate M), and a small flow rate (flow rate L). Therefore, in the embodiment, the flow rate of the air pump is switched to three stages, that is, the flow rate H, the flow rate M, and the flow rate L.

The overall control section 61 controls the pressurized air supply flow rate adjusting unit 38 and the light source control section 60 based on input signals of various operation instructions from the operation panel 12a. The operation panel 12a includes the light amount adjusting section 62, the gas delivery amount adjusting section 63, the power switch 64, and the pump switch 65. Accordingly, it is possible to continuously change the light amount or gradually change the gas supply amount based on the instruction input from the operation panel 12a.

The carbon dioxide gas supply device 13 includes a carbon dioxide gas cylinder 50, a carbon dioxide gas supply flow rate adjusting unit 51, and a check valve 75. The carbon dioxide gas cylinder 50 and the carbon dioxide gas supply flow rate adjusting unit 51 are connected to each other through a gas supply tube 52a. The check valve 75 is connected to the conduit connection connector 45 (refer to FIG. 1) through the gas supply tube 52b.

The gas switching control section 19 is configured inside a control section 71 of the processor 15, controls the carbon dioxide gas supply device 13 and the pressurized air supply device 18, and delivers any one of the pressurized air and the carbon dioxide gas to the conduit connection portion 36b (refer to FIG. 1). At the time of switching a gas using the gas switching control section 19, the supply flow rate setting value of the other of the pressurized air and the carbon dioxide gas supplied to the conduit connection portion 36b before the switching is used. For this reason, the gas switching control section 19 includes a memory (a supply flow rate setting value storing section) 19a. The memory 19a stores the current supply flow rate setting value in the pressurized air supply flow rate adjusting unit 38 and the gas supply flow rate adjusting unit 51. Then, at the time of switching to one of the carbon dioxide gas and the pressurized air and supplying one of them, the supply flow rate setting value before the switching is read out for use from the memory 19a. In this manner, when the gas switching control section 19 is configured through software using the control section 71 of the processor 15, the configuration becomes simple since it is not necessary to further provide a new controller.

As shown in FIG. 3, the gas supply flow rate adjusting unit 51 includes a decompressing mechanism 53, a flow rate control valve 54, pressure gauges 55a and 55b, a gas supply control section 56, and an operation panel 13a. The decompressing mechanism 53, the flow rate control valve 54, and the check valve 75 are connected to each other in series in an order from the gas cylinder 50, and the carbon dioxide gas from the gas cylinder 50 is delivered to the conduit connection connector 45 through the gas supply tube 52b.

The decompressing mechanism 53 is configured as two regulators (decompressing valves) 53a and 53b disposed in series. The regulators 53a and 53b decreases the pressure of the carbon dioxide gas from the gas cylinder 50 in two stages, so that it becomes a pressure safe for a human body. For example, in the first regulator 53a, the pressure of the carbon dioxide gas inside the carbon dioxide gas cylinder 50 is decreased from 10 MPa to 0.3 MPa. Furthermore, in the second regulator 53a, the pressure of the carbon dioxide gas is decreased from 0.3 MPa to 0.05 MPa.

The inlet sides of the regulators 53a and 53b are respectively provided with the pressure gauges 55a and 55b. The pressure gauges 55a and 55b measure the pressure before and after the first-stage regulator 53a. The pressure signals from the pressure gauges 55a and 55b are transmitted to the gas supply control section 56.

The gas supply control section 56 detects a variation in the output pressure from the carbon dioxide gas cylinder 50 based on the pressure signals from the two pressure gauges 55a and 55b, controls the flow rate control valve 54, and displays a remaining amount and an alarm. First, the gas supply control section detects the supply flow rate and the remaining amount of the carbon dioxide gas of the gas cylinder 50 based on the detected pressures from the pressure gauges 55a and 55b. Then, the gas supply control section displays the remaining amount of the detected carbon dioxide gas on the remaining amount display section 57. Furthermore, when the remaining amount of the gas becomes a predetermined level or less, the gas supply control section displays an alarm on an alarm display section 58, and generates an alarm sound. Furthermore, when the output pressure of the carbon dioxide gas becomes a predetermined level or less, the gas supply control section stops the supply of the carbon dioxide gas by controlling the flow rate control valve 54, and supplies the pressurized air from the air pump 41.

The operation panel 13a includes the remaining amount display section 57, the alarm display section 58, and a valve control switch 73, and is connected to the gas supply control section 56. The valve control switch 73 inputs an instruction signal for turning on or off the flow rate control valve 54 by the operation of the surgical operator. This instruction signal is transmitted to the gas supply control section 56, and the flow rate control valve 54 is turned on or off based on the signal.

The flow rate control valve 54 is configured as an electromagnetic proportional valve, and adjusts the flow rate of the carbon dioxide gas passing through the decompressing mechanism 53. The flow rate control valve 54 is controlled by the gas supply control section 56, and as in the ejection flow rate of the air pump 41, the flow rate is switched to three stages, that is, a large flow rate (flow rate H), a middle flow rate (flow rate M), and a small flow rate (flow rate L). The flow rate of the outlet of the flow rate control valve 54 is made equal to the ejection flow rate of the air pump 41 by the gas supply control section 56.

The gas supply flow rate adjusting unit 51 and the pressurized air supply device 18 are selectively driven by the gas switching control section 19 of the processor 15. Therefore, the pressurized air and the carbon dioxide gas are selectively supplied without being simultaneously supplied. Furthermore, the flow rates of the pressurized air and the carbon dioxide gas may be individually adjusted.

As described above, there are provided two gas supply systems, that is, the pressurized air generated by driving the air pump 41 and the carbon dioxide gas supplied from the carbon dioxide gas cylinder 50. Then, either the gas supply control section 56 or the overall control section 61 of the light source device 12 is selected by the gas switching control section 19, and either the pressurized air or the carbon dioxide gas is used. In the embodiment, from the viewpoint of alleviating the burden on the subject, the carbon dioxide gas is first supplied, and the pressurized air is accessorily used.

For this reason, in the initial setting, the gas switching control section 19 drives the gas supply control section 56 so that the carbon dioxide gas is first supplied. Then, for example, when the remaining amount of the carbon dioxide gas inside the carbon dioxide gas cylinder 50 reaches a state where the carbon dioxide gas cannot be supplied any more, the carbon dioxide gas cannot be supplied due to breakage or the like, or the pressurized air is selected to be supplied by the surgical operator, the supply of the carbon dioxide gas from the carbon dioxide gas cylinder 50 to the gas supply tube 52b is stopped. Furthermore, the air pump 41 is driven at the same time when the supply of the carbon dioxide gas is stopped, so that the pressurized air is supplied. Furthermore, in the case of the operation of the surgical operator, the carbon dioxide gas is switched to the pressurized air in a manner such that the valve control switch 73 of the carbon dioxide gas supply device 13 is turned off and the pump switch 65 of the light source device 12 is turned on.

The gas delivery amount adjusting section 63 includes the operation button (or the operation handle), and changes the gas delivery amount in three stages through a push operation or a rotation operation. The gas delivery amount instruction signal input from the gas delivery amount adjusting section 63 is transmitted to the pump driving circuit 42 through the overall control section 61 and is further transmitted to the gas supply control section 56 through the gas switching control section 19 of the processor 15. For this reason, the gas switching control section 19 includes the memory 19a. The memory 19a stores a gas delivery amount instruction value (any of H, M, and L). When a new value is set, the storage value is updated to the new value. Then, the rotation number control section 43 or the flow rate control valve 54 is controlled to become the updated value.

The gas supply control section 56 is connected to the light source device 12 through the gas switching control section 19 of the processor 15. The processor 15 includes a signal processing circuit 70 and the control section 71. The control section 71 is electrically connected to the overall control section 61 of the light source device 12 in order to control, for example, an iris. Furthermore, the gas supply control section 56 of the carbon dioxide gas supply device 13 is electrically connected to the overall control section 61 through the control section 71 of the processor 15. Furthermore, the gas supply control section 56 may be directly connected to the overall control section 61 without using the processor 15.

In use, as shown in FIG. 1, the light source connection portion 36a of the connector 36 of the universal cord 22 is connected to the tube sleeve 12b of the light source device 12. Furthermore, the multi-conduit 44 is connected to the conduit connection portion 36b through the conduit connection connector 45. In this state, when the power switch 64 provided in the operation panel 2a of the light source device 12 is turned on, the respective devices enter an operation state. Here, the gas switching control section 19 controls the gas supply control section 56 so that the carbon dioxide gas from the carbon dioxide gas cylinder 50 is first supplied to the liquid delivery device 14 and the gas supply tube 33.

When the surgical operator operates the gas/water delivery valve 30 of the main body manipulation section 20 in the case where the insertion section 21 is inserted into the body cavity to expand the inside of the body cavity or clean the observation window 24, the carbon dioxide gas is supplied into the body cavity. Then, when the surgical operator operates the gas delivery amount adjusting section 63 of the operation panel 12a, the flow rate of the delivered gas may be switched to any one of the flow rate H, the flow rate M, and the flow rate L. Furthermore, the initial setting is set such that the flow rate of the delivered gas is set to be the flow rate H at the time of starting the endoscope system 10. Therefore, the gas delivery amount adjusting section 63 is operated when decreasing or increasing the flow rate of the delivered gas.

Figure 5:
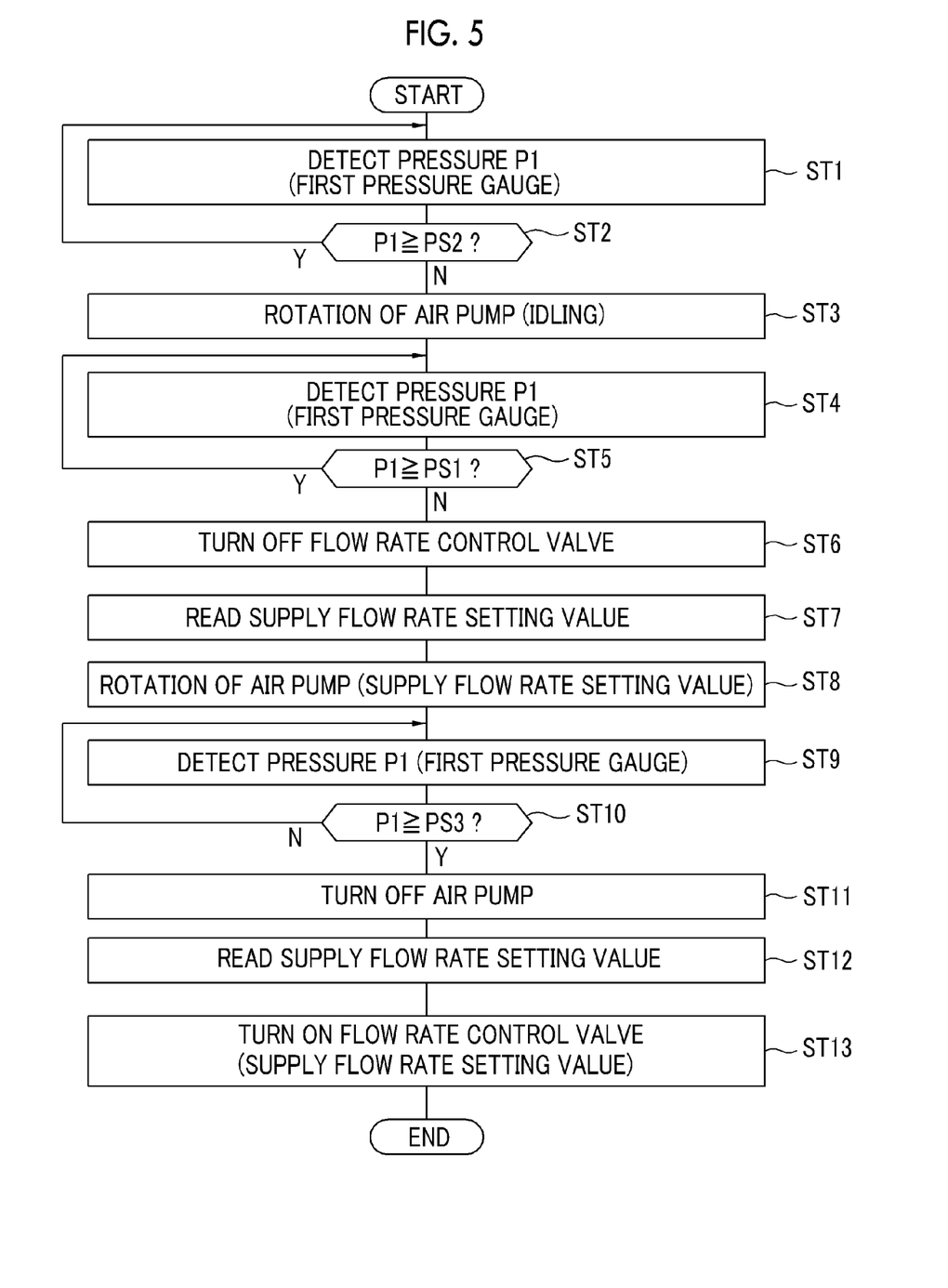
FIG. 5 is a flowchart illustrating a process of switching the supply of a gas based on a variation in the remaining amount of a carbon dioxide gas cylinder.
Figure 6:
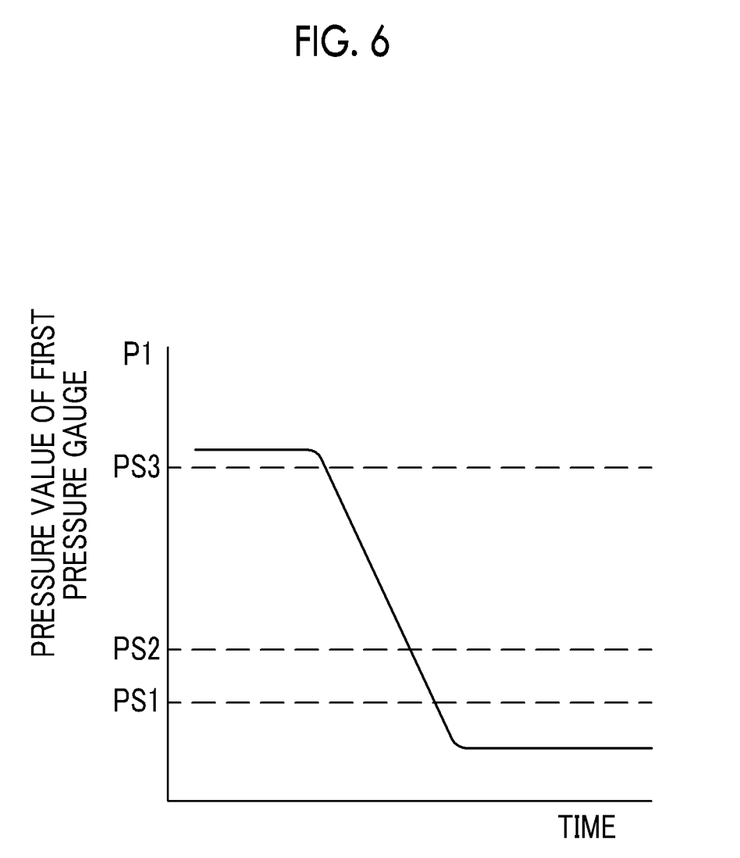
FIG. 6 is a graph illustrating a relationship between a threshold value and a variation in the pressure of a first pressure gauge.

As shown in FIGS. 5 and 6, when the carbon dioxide gas is supplied so that the carbon dioxide gas inside the carbon dioxide gas cylinder 50 is consumed, the internal pressure decreases, so that the carbon dioxide gas cannot be supplied. In order to detect such a supply disabled state in advance, the pressure P1 of the first pressure gauge 55a is detected at regular intervals, for example, every 3 seconds (ST1). Then, when the detected pressure P1 is a second threshold value PS2 (for example, a predetermined value within the range from 0.4 to 0.5 Pa, for example, 0.45 Pa) or more, the current step returns to ST1, so that the pressure P1 is detected every 3 seconds. Furthermore, when the detected pressure P1 becomes less than the second threshold value PS2 (ST2), the air pump 41 is idly rotated (ST3). When the air pump 41 is idly rotated, a small amount of gas is delivered, so that the pressurized air is not delivered to the gas supply tube 33 or the liquid delivery tank 14a.

The pressure P1 of the first pressure gauge 55a is detected for a predetermined time, for example, every 3 seconds (ST4), and the current step returns to ST4 when the detected pressure P1 is the first threshold value PS1 (PS1<PS2) or more. Then, when the detected pressure P1 of the first pressure gauge becomes less than the first threshold value PS1 (ST5), the flow rate control valve 54 is turned off (ST6). Subsequently, the current supply amount is read from the memory 19a of the processor 15 (ST7), the supply amount is set as a new flow rate of the air pump 41 by the rotation number control section 43, and the air pump 41 is rotated at the rotation number to start the gas delivery operation (ST8). Therefore, the same amount of pressurized air as that of the carbon dioxide gas supply device 13 is delivered to the gas supply tube 33 or the liquid delivery tank 14a. In this manner, since the same amount of pressurized air is supplied as the supply flow rate of the carbon dioxide gas before the switching, the operation may be continuously performed, and no discomfort is caused by a variation in the flow rate during the delivery of the gas or the water. For example, when the supply flow rate of the carbon dioxide gas is a flow rate L and the air pump 41 is selected afterward, the ejection flow rate of the air pump 41 becomes the flow rate L. For this reason, since it is possible to prevent a situation in which the pressurized air is supplied at the flow rate H, it is possible to safely and reliably perform the gas switching process.

The first threshold value PS1 is a value used to detect in advance a state where the remaining amount of the carbon dioxide gas cylinder 50 decreases and the delivery gas cannot be supplied, and is determined based on the pressure of the delivery gas.

The pressure P1 is continuously detected by the first pressure gauge 55a every 3 seconds (ST9). When the detected pressure P1 of the first pressure gauge 55a is less than a third threshold value PS3 (PS3>PS2), the current step returns to ST9, so that the pressure P1 is continuously detected (ST9). Then, when the empty carbon dioxide gas cylinder 50 is separated and a new carbon dioxide gas cylinder 50 is attached, the detected pressure P1 of the first pressure gauge 55a becomes the third threshold value PS3 or more (ST10), and the air pump 41 is turned off (ST11). Subsequently, the current supply flow rate setting value is read out from the memory 19a (ST12), and the flow rate control valve 54 is turned on (ST13). Then, the flow rate control valve 54 is controlled by the gas supply control section 56 so that the current flow rate becomes the supply flow rate setting value. Therefore, a new carbon dioxide gas is supplied, and the supply flow rate thereof is equal to that of the supplied pressurized air without any change.

Furthermore, it is possible to switch to the pressurized air supply state using the air pump 41 from the state where the carbon dioxide gas is intentionally supplied by the operation of the surgical operator. In this case, the valve control switch 73 of the carbon dioxide gas supply device 13 is pushed down to be turned off. Subsequently, the pump switch 65 of the light source device 12 is turned on from the off state.

As described above, since the surgical operator may operate the endoscope 11 without paying attention to the remaining amount of the carbon dioxide gas, the operability improves. Furthermore, in addition to the automatic switching, the amount of the delivered gas may be adjusted or switched through the operation of the operation panel 12a of the light source device 12. Furthermore, although two types of gases, that is, the carbon dioxide gas and the pressurized air may be supplied, the carbon dioxide gas is first delivered, and the supply of the pressurized air is accessorily or selectively performed. Furthermore, the manual switching operation between the carbon dioxide gas and the pressurized air may be performed by the light amount adjusting section 62 adjusting the light amount of the light source lamp 40 and the operation panel 12a of the light source device 12, and the operation may be easily performed.

Figure 7:
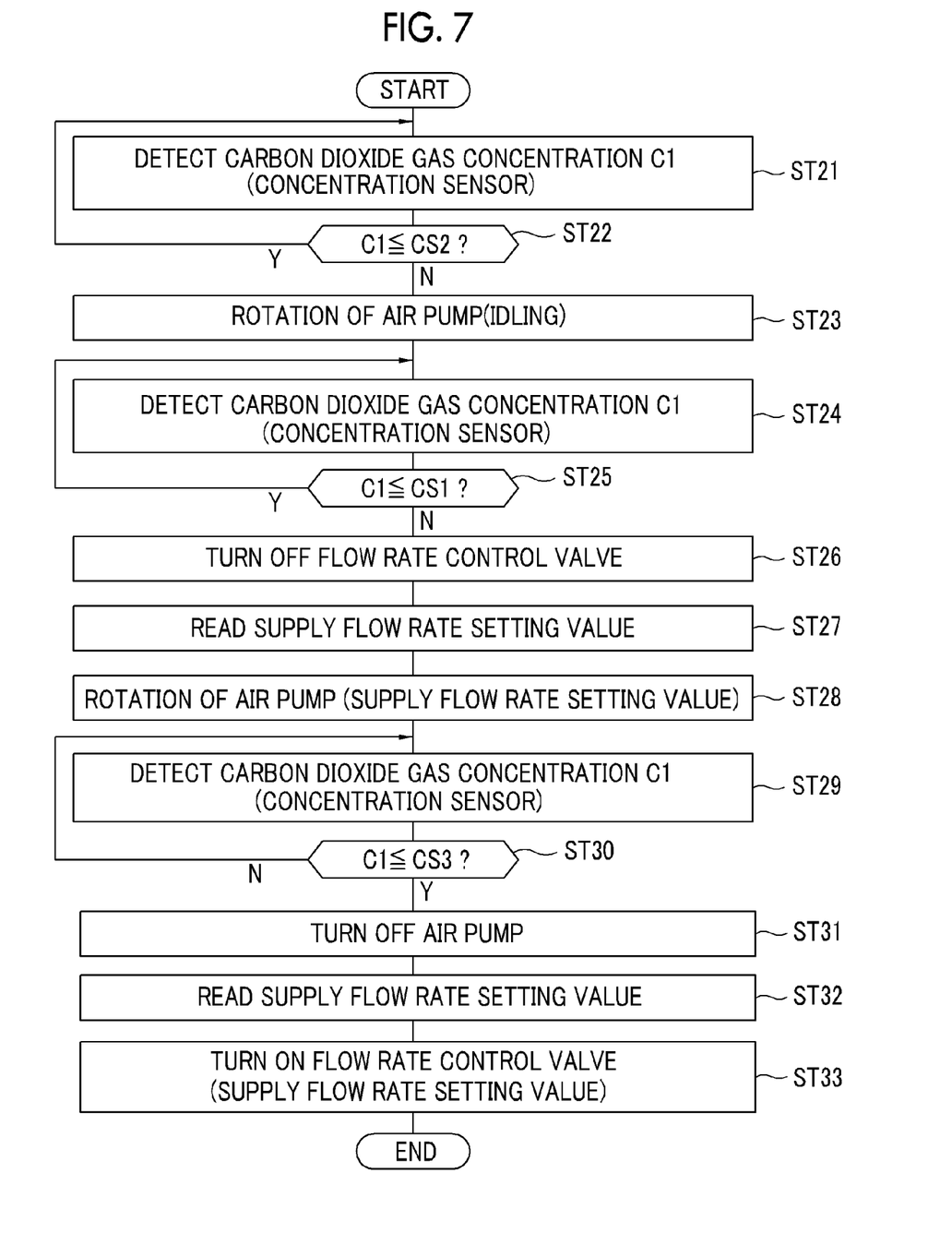
FIG. 7 is a flowchart illustrating a process of switching the supply of a gas based on a variation in the concentration of a carbon dioxide gas.
Figure 8:
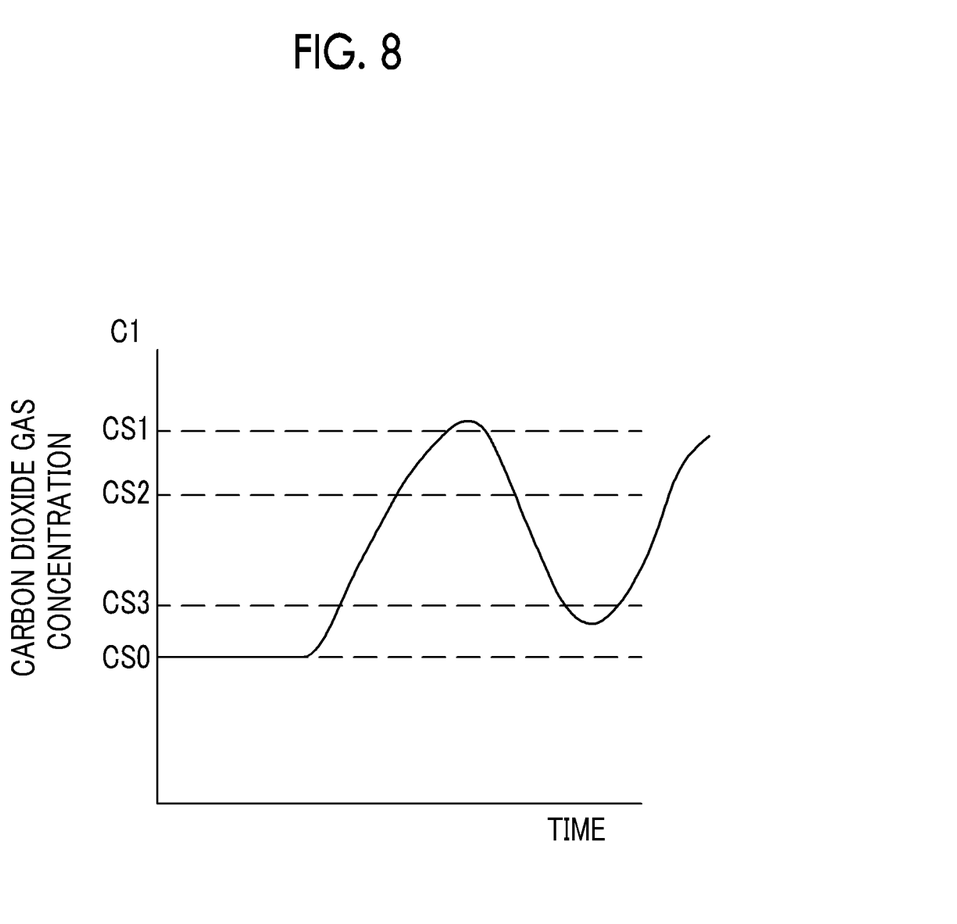
FIG. 8 is a graph illustrating a relationship between a threshold value and a variation in the concentration of a peripheral carbon dioxide gas.

Subsequently, a case will be described in which the switching is automatically performed while the supply of the carbon dioxide gas is stopped and the pressurized air is supplied instead of the automatic switching due to a decrease in the remaining amount or the intentional switching of the surgical operator. For example, when the concentration of the peripheral carbon dioxide gas increases to become a predetermined value or more during the examination and the treatment using the endoscope 11, the automatic switching may be performed. In this case, as shown in FIG. 3, a carbon dioxide gas concentration sensor 76 detecting the concentration of the peripheral carbon dioxide gas is provided, and is connected to the gas switching control section 19 of the processor 15. Then, as shown in FIGS. 7 and 8, when the concentration of the carbon dioxide gas detected by the concentration sensor 76 becomes more than a predetermined concentration, the carbon dioxide gas is switched to the pressurized air. Even in this switching, the supply amount before the switching is read out from the memory 19a so that the supply amount of the carbon dioxide gas before the switching becomes equal to the supply amount of the pressurized air after the switching, and the new pressurized air is switched based on the supply amount read out from the memory. Furthermore, instead of or before the automatic switching, an alarm may be generated for the surgical operator so that the surgical operator determines whether the supply state of the pressurized air is switched.

As shown in FIG. 7, first, the concentration of the peripheral carbon dioxide gas is detected by the carbon dioxide gas concentration sensor 76, for example, every 3 seconds (ST21). When the detected concentration C1 of the concentration sensor 76 is a second threshold value CS2 (CS2<CS1) or less, the current step returns to ST21 (ST22). When the detected concentration C1 becomes more than the second threshold value CS2 (ST22), the air pump 41 is idly rotated (ST23).

The detected concentration C1 is detected for a predetermined time, for example, every 3 seconds by the concentration sensor 76 (ST24), and the detected concentration C1 and the first threshold value CS1 are compared with each other (ST25). In ST25, when the detected concentration C1 is the first threshold value CS1 or less, the current step returns to ST24. Then, in ST25, when the detected concentration C1 becomes more than the first threshold value CS1 (ST25), the gas switching control section 19 turns off the flow rate control valve 54 (ST26). Subsequently, the current supply amount is read out from the memory 19a of the processor 15 (ST27), the supply amount is set as a new flow rate of the air pump 41 in the rotation number control section 43, and the air pump 41 is rotated at the rotation number to start the gas delivery operation (ST28). Therefore, the same amount of pressurized air as that of the carbon dioxide gas supply device 13 is delivered to the gas supply tube 33 or the liquid delivery tank 14a. In this manner, since the same amount of pressurized air is supplied as the supply flow rate of the carbon dioxide gas before the switching, the operation may be continuously performed, and no discomfort is caused by a variation in the flow rate during the delivery of the gas or the water.

Subsequently, the carbon dioxide gas concentration C1 is detected by the carbon dioxide gas concentration sensor 76 (ST29), and the detected concentration C1 and the third threshold value CS3 are compared with each other (ST30). When the detected concentration C1 becomes more than the third threshold value CS3, the current step returns to ST29. Furthermore, when the detected concentration C1 becomes the third threshold value CS3 or less (ST30), the air pump 41 is stopped (ST31), and the flow rate control valve 54 is turned on (ST33). Since the flow rate control valve 54 controls the current flow rate to become the supply flow rate based on the setting value from the memory 19a (ST32), the carbon dioxide gas is supplied at the supply flow rate before the switching. The third threshold value CS3 (CS3<CS2) is a value used to determine whether the carbon dioxide gas may be used. For example, a half of the second threshold value CS2 is used, but the third threshold value is not limited thereto, and may be appropriately changed. Furthermore, the CS0 of FIG. 8 indicates the concentration of the carbon dioxide gas in a normal state before using the carbon dioxide gas under the environment where the endoscope system is used.

Instead of the concentration of the carbon dioxide gas obtained by the carbon dioxide gas concentration sensor around the surgical operator or in addition to the concentration of the carbon dioxide gas, the carbon dioxide gas and the pressurized air may be switched based on the concentration of the carbon dioxide gas inside the body cavity. In this case, the carbon dioxide gas concentration sensor is provided to be disposed inside the clamp insertion channel near the clamp outlet. Furthermore, the concentration of the carbon dioxide gas in blood of the subject is acquired on-line from the device monitoring the state of the subject, and when the concentration of the carbon dioxide gas becomes more than a predetermined value based on the concentration of the carbon dioxide gas as described above, the carbon dioxide gas may be switched to the pressurized air. Furthermore, the carbon dioxide gas concentration sensor may be attached to a portion other than the clamp insertion channel.

Figure 9:
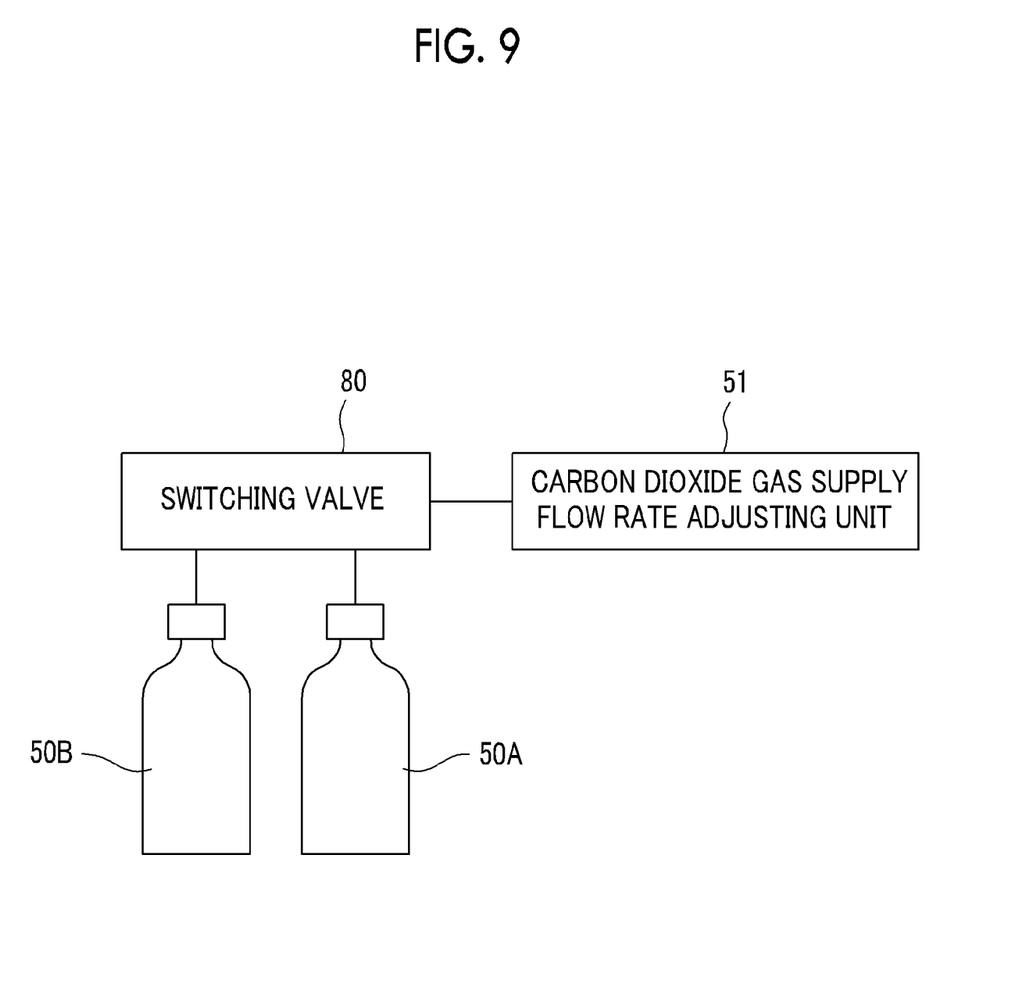
FIG. 9 is a schematic diagram illustrating another embodiment using two carbon dioxide gas cylinders.

In the above-described embodiment, a case has been described in which one carbon dioxide gas cylinder 50 is provided, but as shown in FIG. 9, two carbon dioxide gas cylinders 50A and 50B may be connected to a switching valve 80. Accordingly, it is possible to continuously supply the carbon dioxide gas by switching to the other carbon dioxide gas cylinder when the remaining amount of one carbon dioxide gas cylinder is small. Furthermore, the switching of the carbon dioxide gas cylinder may be manually performed and may also be automatically performed by switching the switching valve when the remaining amount detected by the carbon dioxide gas remaining amount detecting section is a predetermined value or less.

In the above-described embodiment, the operation of switching to the carbon dioxide gas or the pressurized air based on the concentration signal of the carbon dioxide gas using the concentration sensor has been performed together with the switching operation based on the remaining amount of the carbon dioxide gas cylinder, but each of these switching operations may be solely used in the endoscope gas delivery system.

The carbon dioxide gas supply device 13 and the pressurized air supply device 18 may adjust the flow rate in multiple stages other than three stages or may continuously adjust the flow rate in a single stage. Even in this case, when the supply flow rate setting value before the switching is stored on the memory 19a and the supply flow rate setting values of the carbon dioxide gas supply device and the pressurized air supply device are made equal to each other based on the supply flow rate setting value, the carbon dioxide gas and the pressurized air may be switched without any discomfort.

In the above-described embodiment, an example of switching to the pressurized air or the carbon dioxide gas has been described, but the gas supplied by the gas cylinder is not limited to the carbon dioxide gas, and may be another gas, for example, a helium gas.

What is claimed is:

1. An endoscope gas delivery system delivering a gas from a conduit connection portion connected with a gas supply tube of a universal cord to an endoscope including an insertion section inserted into a body of a subject, a main body manipulation section continuous to the insertion section, and the universal cord connected to the main body manipulation section, the endoscope gas delivery system comprising:
    a pressurized air supply device comprising an air pump that generates a pressurized air and supplies the pressurized air to the conduit connection portion;
    a pressurized air supply flow rate adjusting unit that adjusts a supply flow rate of the pressurized air by controlling the air pump;
    a gas cylinder that supplies a gas to the conduit connection portion;
    a depressurizing mechanism that depressurizes the gas;
    a flow rate control valve that is provided adjacent to an outlet of the depressurizing mechanism and adjusts a flow rate of the gas;
    a gas supply control section that controls the flow rate control valve;
    a pressure gauge that is provided adjacent to an inlet of the depressurizing mechanism, measures a pressure of the gas and transmits a pressure signal which indicates an output pressure of the gas to the gas supply control section; and
    a gas switching control section that controls the pressurized air supply flow rate adjusting unit and the gas supply control section, delivers one of the pressurized air and the gas to the conduit connection portion, and performs a switching control using a supply flow rate setting value of the other of the pressurized air and the gas before the switching,
    wherein when the pressure of the pressure gauge becomes a first value PS1, the gas supply control section transmits a gas switching signal to the gas switching control section, and
    when the gas switching control section receives the gas switching signal, the gas switching control section controls the flow rate control valve by controlling the gas supply control section in order to stop the supply of the gas, and drives the air pump by controlling the pressurized air supply flow rate adjusting unit to switch the gas to the pressurized air automatically which is supplied to the conduit connection portion.

2. The endoscope gas delivery system according to claim 1, further comprising:
    a supply flow rate setting value storing section that stores the supply flow rate setting value of the pressurized air supply flow rate adjusting unit and the supply flow rate setting value of the gas supply control section,
    wherein the gas switching control section performs the switching by reading out the supply flow rate setting value before the switching from the supply flow rate setting value storing section.

3. The endoscope gas delivery system according to claim 2, wherein the depressurizing mechanism includes:
    a first depressurizing valve and a second depressurizing valve that are connected to each other in series.

4. The endoscope gas delivery system according to claim 3, wherein when the pressure of the pressure gauge becomes a second value PS2 (PS2>PS1), the gas supply control section idly rotates the air pump.

5. The endoscope gas delivery system according to claim 2, wherein the pressurized air supply flow rate adjusting unit includes a pump driving circuit that controls the rotation number of the air pump.

6. The endoscope gas delivery system according to claim 2, further comprising:
    a concentration sensor that detects the concentration of the carbon dioxide gas,
    wherein when the concentration of the concentration sensor becomes a first value CS1, a gas switching signal is transmitted to the gas switching control section, and the gas switching control section turns off the flow rate control valve and drives the air pump to switch the carbon dioxide gas to the pressurized air.

7. The endoscope gas delivery system according to claim 6, wherein when the detected concentration of the concentration sensor becomes a second value CS2 (CS2<CS1), the gas supply control section idly rotates the air pump.

8. The endoscope gas delivery system according to claim 7, wherein when the detected concentration of the concentration sensor becomes a third value CS3 (CS3<CS2), the gas supply control section transmits a gas switching signal to the gas switching control section, stops the air pump, and turns on the flow rate control valve.

9. The endoscope gas delivery system according to claim 2, further comprising:
    an imaging unit that is disposed to face an observation window of a front end of the insertion section; and
    a processor that receives an image signal from the imaging unit, performs an image process on the imaging signal, and displays the result on a monitor,
    wherein a control section of the processor constitutes the gas switching control section.

10. The endoscope gas delivery system according to claim 1,
    wherein the gas is a carbon dioxide gas, and the gas cylinder is first used at an initial setting.

11. The endoscope gas delivery system according to claim 10, further comprising:
    a concentration sensor that detects the concentration of the carbon dioxide gas,
    wherein when the detected concentration of the concentration sensor becomes a first value CS1, a gas switching signal is transmitted to the gas switching control section, and the gas switching control section turns off the flow rate control valve and drives the air pump to switch the carbon dioxide gas to the pressurized air.

12. The endoscope gas delivery system according to claim 11,
    wherein when the detected concentration of the concentration sensor becomes a second value CS2 (CS2<CS1), the gas supply control section idly rotates the air pump.

13. The endoscope gas delivery system according to claim 12,
    wherein when the detected concentration of the concentration sensor becomes a third value CS3 (CS3<CS2), the gas supply control section transmits a gas switching signal to the gas switching control section, stops the air pump, and turns on the flow rate control valve.

14. The endoscope gas delivery system according to claim 1,
    wherein the depressurizing mechanism includes:
    a first depressurizing valve and a second depressurizing valve that are connected to each other in series.

15. The endoscope gas delivery system according to claim 14,
   wherein when the pressure of the pressure gauge becomes a second value PS2 (PS2>PS1), the gas supply control section idly rotates the air pump.

16. The endoscope gas delivery system according to claim 1,
   wherein the pressurized air supply flow rate adjusting unit includes a pump driving circuit that controls the rotation number of the air pump.

17. The endoscope gas delivery system according to claim 1, further comprising:
   an imaging unit that is disposed to face an observation window of a front end of the insertion section; and
   a processor that receives an image signal from the imaging unit, performs an image process on the imaging signal, and displays the result on a monitor,
   wherein a control section of the processor constitutes the gas switching control section.

18. The endoscope gas delivery system according to claim 1,
   wherein the conduit connection portion forms a chamber between the conduit connection portion and a conduit connection connector, and includes a relief valve communicative connected with the chamber and releasing a gas when the pressure of the chamber becomes a predetermined pressure or more.

* * * * *